(12) United States Patent
Hodgen

(10) Patent No.: US 7,256,185 B1
(45) Date of Patent: Aug. 14, 2007

(54) CONTROL OF SELECTIVE ESTROGEN RECEPTOR MODULATORS

(75) Inventor: Gary D. Hodgen, Virginia Beach, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 628 days.

(21) Appl. No.: 09/313,628

(22) Filed: May 18, 1999

Related U.S. Application Data

(60) Division of application No. 09/059,476, filed on Apr. 13, 1998, which is a continuation-in-part of application No. 08/888,183, filed on Jul. 3, 1997, now abandoned.

(51) Int. Cl.
*A61K 31/56* (2006.01)
*A61K 31/135* (2006.01)

(52) U.S. Cl. ............... 514/171; 514/182; 514/650

(58) Field of Classification Search ......... 514/171, 514/178, 179, 324, 651, 182, 650
See application file for complete search history.

(56) References Cited

U.S. PATENT DOCUMENTS 4,133,814 A * 1/1979 Jones et al. ............ 548/525
4,900,815 A * 2/1990 Tanaka et al.
5,646,137 A * 7/1997 Black et al.
5,721,278 A * 2/1998 Garfield .................. 514/652

OTHER PUBLICATIONS

Basu, Jayasree, 79CA:210, Dec. 1973.*
Schane et al, 90CA:16759, Dec. 1978.*
Jones et al, 90CA:151974, Jan. 9, 1979*
The Merck Manual of Medicial Information, Home Edition, Berkow et al Eds. Pocket Books, New York, 1997, p. 1225.*
Basu, J. "Antifertility Effect of Three New Clomiphene Analogue on Animals" 1972, Jap. J. Exp. Med, 9-15.*
Schane et al. "Fertility in the rhesus monkey following long-term inhibition of ovarian function with danazol" 1978, Fertil. Steril. 29(6), 692-4.*

* cited by examiner

*Primary Examiner*—San-Ming Hui
(74) *Attorney, Agent, or Firm*—Dickstein Shapiro LLP

(57) ABSTRACT

The treatment of an estrogen sensitive condition by the administration of a selective estrogen receptor modulator is improved by additionally administering a progestationally active compound to the recipient. The additional agent can express both progestational and androgenic activity or an androgenically active material can be employed, if desired. Additionally, clomiphene in an array of isomeric ratios (EN:ZU) can be used alone for prevention of osteoporosis, maintenance of a healthful blood lipid profile, and prevention of breast tumors, or to sustain amenorrhea.

13 Claims, No Drawings

CONTROL OF SELECTIVE ESTROGEN RECEPTOR MODULATORS

This is a divisional of application Ser. No. 09/059,476, filed Apr. 13, 1998 which is a continuation-in-part of application Ser. No. 08/888,183, filed Jul. 3, 1997 and now abandoned.

BACKGROUND OF THE INVENTION

The use of estrogens in the course of treatment of a variety of conditions is well known. For example, the most prevalent form of oral contraception is the so-called combined oral contraceptive preparation, a pill that combines both estrogen and a progestin. Apparently, the progestin acts foremostly to block gonadotropin release while the estrogen component primarily provides endometrial control to diminish breakthrough bleeding. Another well-known use is long term estrogen replacement therapy which is common for post-menopausal and other estrogen deficient women. Other estrogen dependent conditions include endometriosis, uterine fibroid tumors (leiomyomata), pre-menstrual syndrome, dysfunctional uterine bleeding, breast tumors (benign and malignant) and the like.

Despite their value, estrogen treatments are also associated with undesirable side effects. For example, estrogen therapy has been associated with an increased incidence of endometrial cancer, especially due to the continual "unopposed" estrogen-induced proliferation of the endometrium. Other side effects include uterine bleeding and cyclotherapeutic withdrawal menstrual bleeding during a time in their lives when many women welcome cessation of menstrual bleeding as a normal occurrence in menopause. Estrogen therapy has also been implicated in the development of a variety of disorders including gallbladder disease, hypertension, abnormal glucose tolerance, hypercoagulable states and breast cancer, although some of these observations are antidotal in nature and have not been confirmed.

There have been numerous efforts to counteract the ill effects of estrogen therapy. For instance, attempts have been made to couple estrogen therapy with short periods of anti-estrogen supplementation. Another approach is to use anti-estrogens in place of the estrogen. Certain compounds are known as "anti-estrogens" because they can bind to the estrogen receptors and competitively block the binding of the more potent estrogens such as estradiol. Among the best known of these anti-estrogens are clomiphene and tamoxifen. However, all such anti-estrogens can be, in fact, active estrogens depending on the tissue, dose/regimen and hormonal milieu of the drug exposure. These are mixed function agonistic/antagonistic activities. The degree to which the anti-estrogen acts as an estrogen also depends on the particular material and the tissue site.

While anti-estrogen therapy has been successful, it is not without its own problems. As is know, there is a hypothalamic-pituitary-gonadal axis involved in endogenous hormone production. As estrogen binds to its receptors, there is a feedback mechanism which regulates the endogenous production of pituitary gonadotropins and, in turn, estrogen so that the hormonal milieu remains within the physiological range. When an anti-estrogen binds to the estrogen receptors, altered estrogen feedback mechanisms are implicated in a pharmacological manner compared to when estrogen binds normally. The anti-estrogens themselves can induce multiple follicular growth which, in turn, causes the production of endogenous ovarian estrogens. A favorable example is the use of clomiphene for ovulation induction.

For the first anti-estrogen dose administration and continuing for some period of time, the endogenous estrogen produced as a consequence of the multiple follicular growth may not appear to pose a problem. However, at some point, which is totally unpredictable and which varies from individual to individual, endogenous estrogen can be produced such that the quantity of estrogen present can elevate blood levels well above 300 pg/ml. Indeed, estradiol concentration in plasma may exceed a few thousand in some instances. Therefore, while the use of an anti-estrogen seeks to reduce or modify or eliminate the side effects of estrogen, its use over time may have the reverse effect by inducing an excess concentration of estrogen. Not only may the use of the anti-estrogen exaggerate the estrogen side effects which it seeks to avoid, but the anti-estrogen may also even eliminate the primary benefit of the administration in the first instance. For example, a "run away" endogenous estrogen can induce ovulation in those situations where the administration of the anti-estrogen was designed to provide contraception. This feature of anti-estrogen therapy makes the establishment and maintenance of appropriate dosages of anti-estrogen difficult and in some cases impossible, especially when the therapeutic goal is simultaneous to limit excessive estrogenic impact in one tissue, while itself providing adequate estrogenic stimulation in another tissue.

It is therefore the object of the present invention to keep the hypothalamus and pituitary from becoming deranged and thereby prevent multiple follicular growth and the endogenous estrogen sustained, supraphysiological elevations which result from ovarian hyperstimulation. This and other objects of the invention will become apparent to those of ordinary skill in the art from the following detailed description.

SUMMARY OF THE INVENTION

This invention relates to a method of using a SERM such as clomiphene, for instance, pre- and postmenopausally, e.g., in hormone replacement therapy to prevent osteoporosis, cardiovascular disease and breast cancer, as well as preventing the hypothalamus and pituitary from operating in a deranged manner during any SERM therapy. More particularly, the invention involves superposing upon the use of a selective estrogen receptor modulator, the co-administration of a compound progestationally active to women, either of reproductive age women who are pre-menopausal or who are post-menopausal. The progestationally active compound may also exhibit androgenic activity or an androgenically active compound can be coadmistered.

DETAILED DESCRIPTION OF THE INVENTION

In accordance with the present invention, an additional hormonal therapy is superposed upon the use of a selective estrogen receptor modulator (also known as a SERM, selective estrogen or anti-estrogen) in the known use of the SERM, for instance, as in treating or controlling an estrogen sensitive condition. Estrogen sensitive conditions include, but are not limited to, contraception, hormone replacement therapy, endometriosis, leiomyoma, dysfunctional uterine bleeding, premenstrual syndrome, hormonal dependent cancers, such as those of the breast, endometrial and ovarian, and the like. Some SERMs have been indicated for the prevention of post-menopausal osteoporosis, modulation of serum lipid profiles and breast cancer prevention.

Any known SERM can be used in the practice of this invention for its known utility in the treatment or modification of a medial condition in mammals. Examples of known SERMs include, but are not limited to, clomiphene; cycladiene; tamoxifen; nafoxidine; nitromifene citrate (N-55, 945-27); 13-ethyl-17α-ethynl-17β-hydroxygona-4-9-11-trien-3-one (R2323); diphenol hydrochrysene; erythro-MEA; allenolic acid; cyclofenyl; chlorotrianisene; ethamoxytriphetol; triparanol; CI-626; CI-680; MER-25; U-11, 555A; U-11,100A; ICI-46,669; ICI-46,474; CN-55,945; compounds of the formula:

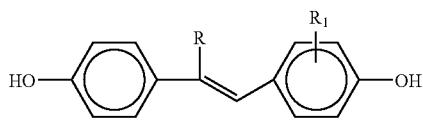

where $R_1$ is hydrogen, an aromatic group or alkyl of preferably no more than nine carbon atoms, R is an aromatic or alkyl group of preferably no more than nine carbon atoms and various of their derivatives; the triphenyl compounds described in U.S. Pat. No. 2,914,563 which are of the formula:

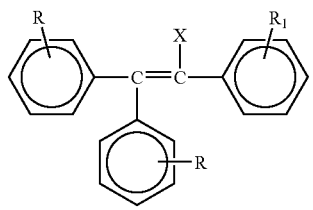

wherein one of the R groups is a basic ether of the formula $OC_nH_{2n}A$ in which n is 2, 3 or 4 and A is a $C_{1-4}$ dialkylamino group, N-piperidyl or β-morpholinyl and the other R and $R_1$ are hydrogen, halogen or methoxy while X is halogen; as well as benzothiophenes such as those described in U.S. Pat. No. 5,624,940 of the formula:

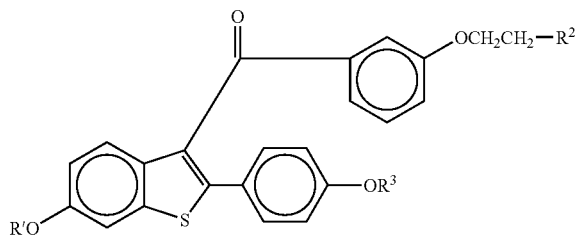

in which $R^1$ and $R^3$ are independently hydrogen, $C_{1-4}$ alkyl, —$CO(C_{1-6}$alkyl) or —COAr in which Ar is optionally substituted phenyl, $R^2$ is pyrrolidino, hexamethyleneamino or piperidino, or a salt thereof. Example of the benzothiophenes include raloxifene (6-hydroxy-2-(4-hydroxyphenyl)-3-[(4-(2-piperidinethoxy)-benzoyl]benzo[b]thiophene) and LY353381.HCl benzothyphenes. The SERMs can also be employed in the form of their pharmaceutical acceptable non-toxic salt or complexes. Examples include the acid addition salt such as, for instance, citrate, hydrochloride, hydrobromide, sulfate, phosphate, nitrate, oxalate, fumarate, gluconate, tannate, maleate, acetate, benzoate, succinate, alginate, malate, ascorbate, tartrate and the like. The complexes can be with metals or various organic moieties.

The SERM aspect of the present invention is similar to the previous use of such materials for the treatment of estrogen dependent or other medical conditions. Thus, not only may any known SERM be employed, but also the dosage amount and mode of administration heretofore employed can also be employed in the practice of the present invention. Those SERMs which have an asymmetric atom can be used as the racemate or in any of the chiral or entomeric forms or mixture of such forms. For example, clomiphene can be used with an array of isomeric ratios (EN:ZU), as well as employing only one of the isomers. Thus, the route of administration can be in any conventional route where the SERM is active, for instance orally, intravenously, subcutaneously, intramuscularly, sublingually, percutaneously, rectally, intranasally or intravaginally. Similarly, the administration form can be a tablet, dragee, capsule, pill, nasal mist, aerosol, pellet, implant (or other depot) and the like.

Superposed on the SERM administration is the use of a progestationally active compound, optionally with androgenic activity or in combination with an androgenically active compound. The additional agent can be progesterone, a synthetic progestin analog or even an anti-progestin having agonistic activity (i.e., progestin-like activity without relying on its "non-competitive anti-estrogenic" properties). Examples of progestins which can be utilized include progesterone, medroxyprogesterone acetate, norgesterel, levo-norgesterol, norethindrone and its esters, norethynodrel, ethynodiol diacetate, chlormadione acetate, cyproterone and its esters, norethindrone, gestodene, desogestrel, norgestimate, and the like. Examples of androgenic compounds include low doses of testosterone, androsteridione and DHT. Some compounds such as danazol and levonorgestrel exhibit both androgenic and progestogenic activity simultaneously.

The antiprogestin can be a progesterone receptor antagonist or any pharmaceutically suitable agent that counteracts the normal biological activity of progesterone. A preferred antiprogestin is a progesterone receptor antagonist. For example, RU 486 is particularly suitable in the practice of this invention.

Examples of antiprogestins which can be employed in this invention are RU 486 ("mifepristone", Roussel Uclaf, Paris; U.S. Pat. No. 4,386,085); and the steroids described in the following patents and patent applications: U.S. Pat. No. 4,609,651, especially the compound lilopristone (11β-(4-dimethylaminophenyl)-17β-hydroxy-17α-(3-hydroxy-prop-1-(Z)-enzyl-4,9(10) estradien-3-one); U.S. application Ser. No. 06/827,050, especially the compounds 11β-(4-acetylphenyl)-17β-hydroxy-17α-(1-propenyl)-4,9-estradien-3-one and 11β-(4-acetylphenyl)-17β-hydroxy-17α-(3-hydroxy-1(2)-propenyl)-4,9-estradien-3-one; U.S. application Ser. No. 07/283,632; U.S. Pat. No. 5,095,129; and other anti-gestations, e.g., U.S. Pat. No. 4,891,368.

Other examples of progestinally active compounds are well known in the art.

The amount of progestationally and optional androgenically active compound which is administered is that which is effective to regulate endogenous estrogen secretions to a desired level. Thereby, ovulation can be blocked and endometrial growth and menstruation can be controlled. As a general proposition, the blood estrogen (endogenous) concentration achieved can be in the range of about 25 to 125 pg/ml and more preferable about 60 to 90 pg/ml, although other values can be selected if desired.

The progestinally and optional androgenically active compound can be administered by way of any art recognized means as practiced in the pharmaceutical arts. For example, it can be formulated in combination with the SERM or separately so that it is administered orally, subcutaneously, intramuscularly, buccally, by a skin patch for transdermal absorption, contained within an inert matrix which is implanted within the body and in the depot state or intravaginally in a matrix that releases the material.

Formulations containing the SERM or the progestationally active and optional androgenically active compound, together with a suitable carrier, can be a solid dosage form which includes tablets, capsules, cachets, pellets, pills, powders and granules; topical dosage forms which include solutions, powders, fluid emulsions, fluid suspensions, semisolids, ointments, pastes, creams, gels or jellies and foams; and parental dosages forms which include solutions, suspensions, emulsions or dry powder. The composition can in addition contain a pharmaceutical acceptable diluents, fillers, disintegrates, binders, lubricants, surfactants, hydrophobic vehicles, water soluble vehicles, emulsifiers, buffers, humeticants, moisturizers, solubilizers, preservatives and other means of augmenting the medicinal entity. The means and methods of administration are known in the art and the artisan can refer to various pharmalogic references for guidance. One such reference is "Modern Pharmaceuticals", Banker & Rhodes, Marcel Dekker, Inc. 1979 and another is Goodman & Gilman's, "The Pharmaceutical basis of therapeutics", 6th Ed., MacMillan Publishing Co., New York, 1980.

If desired, the two (or three) components, namely the SERM and the progestationally active and optional androgenically active compound, can be coadministered utilizing the same or different dosage forms or means, for example for the same tablet. Application of the components, compositions and the methods of this invention for the medical and/or pharmaceutical use which are described in this text can thus be accomplished by any clinical, medical or pharmaceutical methods or techniques as are presently or prospectively known to those skilled in the art.

The administration of the components can be either periodic such as a weekly basis or continuous, that is on a daily administration. Daily administration is preferred because individuals are more likely to follow the treatment regimen and not to forget or overlook a periodic administration schedule. Amounts can be lowered or raised based on the administration regimen and based on the characteristics of the individual receiving the treatment. Variations of dosage based or the route of administration may vary and such changes can be determined practicing known techniques.

The pharmaceutical formulations can be provided in kit form containing a plurality of dosage units intended for ingestion on successive days. Preferably, the plurality is in multiples of seven.

In order to further illustrate the present invention, specific examples are set forth below. It would be appreciated, however, that these examples are illustrative only and are not intended to limit the scope of the invention.

EXAMPLES

1. Clomiphene is used alone at 100 mg/day for the treatment of endometriosis. After 15 days, the serum estrogen reached 500 pg/ml. Levonorgestrel at 75 mcg/day is then also administered. The serum estrogen retreated to physiological value.

2. Raloxifene at 500 mg/day and medroxprogesterone acetate at 12 mg/day were administrated to treat leiomyoma. Serum estrogen remained at physiological levels.

3. Example 1 is repeated using clomiphene EN:ZU isomers in a ratio of 8:1.

4. Clomiphene ZU isomer at 50 mg/day and norgestimate at 100 mcg/day are coadministered while the serum estrogen remained at physiological levels.

5. Clomiphene is used alone at 100 mg/day for the treatment of endometriosis. After 15 days, the serum estrogen reached 500 pg/ml. Danazol at 100 to 800 mg/day is then also administered. The serum estrogen retreated to physiological value.

6. Example 5 is repeated using testosterone at a dosage of 2 to 10 mg/day in place of the danazol.

What is claimed is:

1. In a method of achieving contraception in a premenopausal human female by administering to the female a contraception effective amount of a contraceptive agent, the improvement which comprises said agent being a combination of a contraception effective amount of a Selective Estrogen Receptor Modulator and an agent which exhibits progestogenic activity, wherein the amount of the agent which exhibits progestogenic activity is effective to ameliorate or eliminate the bleeding side effects of the Selective Estrogen Receptor Modulator.

2. The method of claim 1 wherein the Selective Estrogen Receptor Modulator is clomiphene.

3. The method of claim 1 wherein the Selective Estrogen Receptor Modulator is a benzothiophene.

4. The method of claim 1 wherein the agent which exhibits progestogenic activity is an antiprogestin.

5. The method of claim 4 wherein the antiprogestin is a progesterone receptor antagonist.

6. The method of claim 5 wherein the Selective Estrogen Receptor Modulator is clomiphene.

7. The method of claim 5 wherein the Selective Estrogen Receptor Modulator is a benzothiophene.

8. The method of claim 4 wherein the amount of antiprogestin is that sufficient to maintain the blood estrogen concentration in the range of about 25 to 125 pg/ml.

9. The method of claim 8 wherein the amount of antiprogestin is that sufficient to maintain the blood estrogen concentration in the range of about 60 to 90 pg/ml.

10. The method of claim 1 wherein the agent which exhibits progestogenic activity expresses both androgenic and progestogenic activity.

11. The method of claim 10 wherein the agent which exhibits progestogenic activity comprises the combination of an androgen and a progestin.

12. The method of claim 10 wherein the agent which exhibits progestogenic activity is a single material which expresses both activities.

13. The method of claim 12 wherein the agent which exhibits progestogenic activity is danazol or levonorgestrel.

* * * * *